United States Patent [19]

Long et al.

[11] Patent Number: 5,464,844
[45] Date of Patent: Nov. 7, 1995

[54] [3H,7H]THIAZOLE[3,4-A]PYRIDINES HAVING ANTIASTHMATIC AND ANTIINFLAMMATORY ACTIVITIES ON THE RESPIRATORY TRACT

[75] Inventors: Giorgio Long; Giampiero De Cillis; Antonella Rozzi; Simonetta D'Aló; Licia Gallico, all of Milan, Italy

[73] Assignee: Boehringer Mannheim Italia, S.p.A., Milan, Italy

[21] Appl. No.: 244,208

[22] PCT Filed: Dec. 2, 1992

[86] PCT No.: PCT/EP92/02783

§ 371 Date: Jun. 2, 1994

§ 102(e) Date: Jun. 2, 1994

[87] PCT Pub. No.: WO93/11133

PCT Pub. Date: Jun. 10, 1993

[30] Foreign Application Priority Data

Dec. 6, 1991 [IT] Italy ..................... MI91A3270

[51] Int. Cl.⁶ .................... A61K 31/435; C07D 513/04
[52] U.S. Cl. ........................... 514/301; 546/114
[58] Field of Search ................... 546/114; 514/301

[56] References Cited

U.S. PATENT DOCUMENTS 3,948,923 6/1976 Meyer ..................... 260/294.9

FOREIGN PATENT DOCUMENTS 2210633 9/1973 Germany.
8700836 2/1987 WIPO.
9118906 12/1991 WIPO.

OTHER PUBLICATIONS

Dorsch W. and Ring J. Late Phase Reactions. In 'New Trends in Allergy II' edited by Ring J. and Burg, G. Springer Verlag. Germany (1986) pp. 174–197.
Journal of Medicinal Chemistry, vol. 34, No. 7, Jul. 1991, pp. 2248–2260.

Primary Examiner—Ceila Chang
Assistant Examiner—Evelyn Huang
Attorney, Agent, or Firm—Nikaido, Marmelstein, Murray & Oram

[57] ABSTRACT

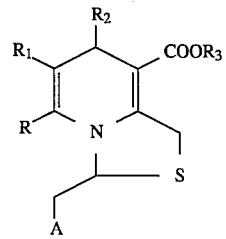

Compounds of formula (I), having antiasthmatic and antiinflammatory actions on the respiratory tract, processes for the preparation thereof and pharmaceutical compositions containing them.

9 Claims, No Drawings

[3H,7H]THIAZOLE[3,4-A]PYRIDINES HAVING ANTIASTHMATIC AND ANTIINFLAMMATORY ACTIVITIES ON THE RESPIRATORY TRACT

This application is the national phase of PCT/EP 92/02783 filed on Dec. 2, 1992.

The present invention relates to [3H,7H]thiazole[3,4-a]pyridines, a process for the preparation thereof and pharmaceutical compositions containing them.

More precisely, the invention relates to compounds of formula (I)

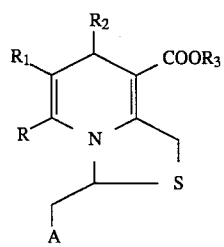

wherein:

R is $(C_1-C_4)$ alkyl;

$R_1$ is a cyano, free or salified carboxy, $(C_1-C_6)$ alkoxycarbonyl group or a group of formula —CONH$(CH_2)_q$NR$_a$R$_b$ wherein q is an integer from 2 to 4;

$R_a$ is hydrogen, $(C_1-C_6)$ alkyl, benzyl; $R_b$ is hydrogen or $(C_1-C_6)$ alkyl or $R_a$ and $R_b$, together with the nitrogen atom, form a pyrrolidino, piperidino, morpholino, 4-thiomorpholino, $(C_1-C_4)$-alkylpiperazino group;

$R_2$ is a $(C_3-C_7)$-cycloalkyl, α-, β-, or γ-pyridyl, optionally substituted phenyl or a bicyclic ring in which a benzene ring is fused to a 5- or 6- membered heterocycle containing one or more heteroatoms selected from O, S, N linked through the benzene ring;

$R_3$ is hydrogen, a pharmaceutically acceptable cation or $(C_1-C_6)$ alkyl;

A is a group of formula:

a) 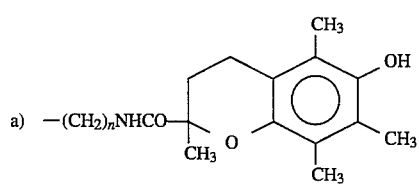

b) 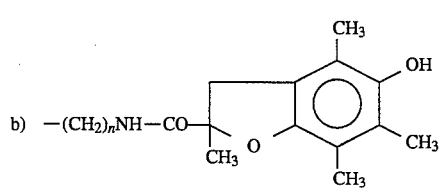

c) 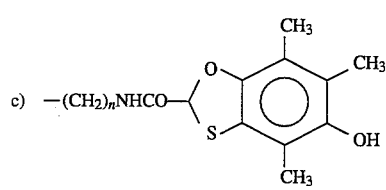

d) 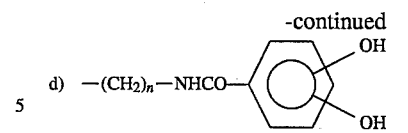

e) 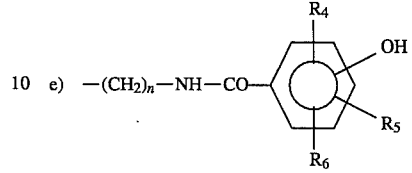

f) 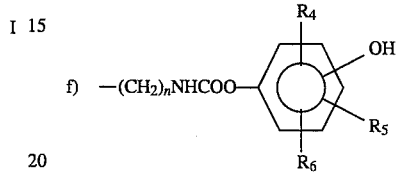

g) 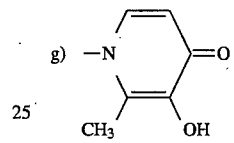

h) 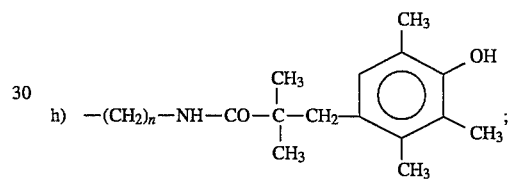

i) —CH$_2$—NH—CO—NRc—OH $R_4$, $R_5$ and $R_6$ are straight or branched $(C_1-C_4)$ alkyl or one of them is hydrogen and the other are straight or branched $(C_1-C_4)$ alkyl; or one of them is —CH$_2$NRaRb, being Ra, Rb as defined above; Rc is $(C_1-C_4)$ alkyl; n is zero or an integer from 1 to 3.

A particularly preferred meaning for n is n=1.

By "optionally substituted phenyl" we mean a phenyl ring containing from 1 to 3 substituents selected from $(C_1-C_6)$ alkyl groups, such as methyl, ethyl, propyl, isopropyl, tert-butyl; $(C_1-C_4)$alkoxy such as methoxy, ethoxy or propoxy; $(C_1-C_4)$ alkylthio such as methylthio, ethylthio; phenoxy; 4-hydroxyphenoxy; phenylthio; 4-hydroxyphenylthio; halogen atoms (chlorine, bromine or fluorine); cyano, azido, nitro, amino groups; $(C_1-C_6)$ acylamino; trihaloacetylamino such as trifluoroacetylamino; methane- or trifluoromethanesulfonamido; benzene- or para-tolylsulfonamido; trihalomethyl such as trichloro- or trifluoromethyl; dihalomethoxy such as difluoromethoxy; trifluoromethoxy; free or salified carboxy; $(C_1-C_4)$alkoxycarbonyl.

Particularly preferred mono and/or polysusbtituted phenyl groups are those bearing the following substituents: 2-chloro-, 3-chloro- , 4-chloro-, 2,3-dichloro-, 2-fluoro-, 2-fluoro-3-chloro-, 2-nitro-, 3-nitro, 3-nitro- 4-phenoxy-, 4-nitro-, 4-nitro-3-phenoxy-, 2-trifluoromethyl-, 3-trifluoromethyl-, 3-cyano-, 3-methoxy-, 2-amino-, 3-amino-, 4-amino-, 2 -methanesulfonamido-, 3-methanesulfonamido-, 4-methanesulfonamido-, 3-methanesulfonamido-4-phenoxy-, 4-methanesulfonamido-3-phenoxy-, 4-fluoro-2,3-dichloro-, 3-carboxy-4-hydroxy-, 3-hydroxy-4-carboxy- and combinations thereof.

When $R_2$ is a $(C_3-C_7)$cycloalkyl, this is preferably cyclopropyl, cyclopentyl or cyclohexyl.

When $R_1$ is an alkoxycarbonyl group, this is preferably a $(C_1-C_4)$alkyl, allyl, propargyl, benzyl, p-methoxy-benzyl, benzhydryl, trityl or trichloroethyl ester.

When $R_2$ is a bicyclic ring in which a benzene ring is fused with a 5- or 6- membered heterocyclic ring, this is preferably benzo-1,3-dioxolane-4-yl, 1,4-benzodioxolane-6-yl, 1,4-benzodioxolane-5-yl, benzofuran-4-yl, benzofurazan-4-yl.

In the groups of formula d), the OH groups are preferably at the 2,3- or 3,4- positions of the phenyl ring.

In the groups of formulae e) and f) the preferred residues of formula

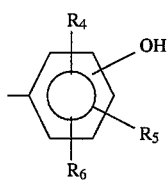

are the following ones:

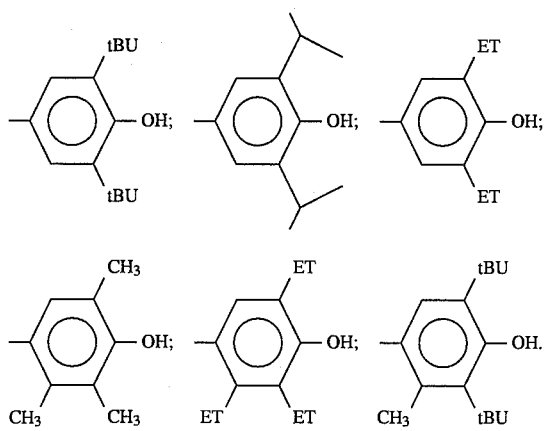

Preferred compounds (I) are those in which $R_1$ is a cyano or alkoxycarbonyl group, particularly methoxycarbonyl, ethoxycarbonyl, allyloxycarbonyl or a group of formula —CONH(CH$_2$)$_q$NRaRb, wherein q, Ra and Rb are as defined above; $R_2$ is an optionally substituted phenyl group or a $(C_3-C_7)$-alkyl group, as defined above; R is methyl and $R_3$ is $(C_1-C_6)$ alkyl.

The most preferred compounds (I) are those in which $R_1$ is an alkoxycarbonyl group; $R_2$ is an optionally substituted phenyl; R is methyl and $R_3$ is $(C_1-C_6)$ alkyl.

When in compounds of formula (I) an acid or basic group is pre sent, this can be salified respectively with pharmaceutically acceptable bases or acids. The resulting non toxic salts are included in the invention, as well as the single enantiomers, the racemates and the diastereomers, or the mixtures thereof. Particularly, compounds of formula (I) contain 2 chiral carbon atoms at the 3 and 7 positions and therefore sin and anti geometries can be defined, corresponding to the following formulae (Ia) and (Ib):

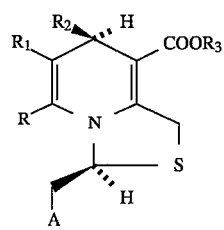

(Ia)-sin

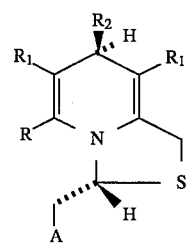

(Ib)-anti

Compounds of formula (Ia) will hereinafter be named sin[3H,7H]thiazole[3,4-a]pyridines or simply [3H,7H]thiazole[3,4-a]pyridines. Compounds of formula (Ib) will be indicated as anti-[3H,7H]thiazole[3,4a] pyridines whereas the diastereomeric mixtures will be named (s,a)-[3H,7H]thiazole[3,4-a]pyridines.

Both compounds of formula (Ia) and those of formula (Ib), obtained from racemic dihydropyridines, are as racemic mixtures. The optically active compounds (Ia) will be indicated as (+)- or (−)-sin-[3H,7H]thiazole[3,4-a]pyridines or simply (+)- or (−)-[3H, 7H]thiazole [3,4-a]pyridines; compounds (Ib) will be named (+)- or (−)-anti-[3H,7H]thiazole [3,4-a]pyridines.

Compounds of formula (I) in which n is 1 are prepared subjecting the compounds of formula (II)

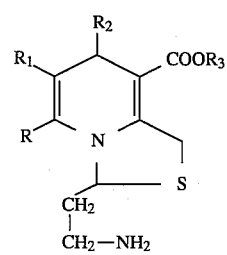

II wherein R, $R_1$, $R_2$ and $R_3$ have the same meanings of formula (I), to one of the following reactions:

a) formation of amides with 6-hydroxy-2,5,7,8-tetra-methyl-chroman- 2-yl carboxylic, hydroxyphenyl- or dihydroxyphenyl-benzoic acids optionally substituted with $R_4$, $R_5$ or $R_6$ alkyl group as defined above or with the acids of formula (III) or (IV)

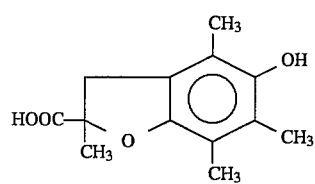

III

-continued

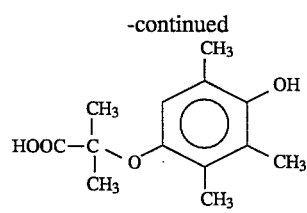
IV or with the corresponding reactive derivatives of said acids;

b) carbonylation with phosgene, carbonyldiimidazole or equivalent reagents, followed by a reaction with a substituted phenol of formula (V)

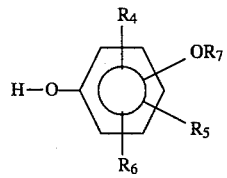
V or with a hydroxylamine of formula HNRc-OH, wherein $R_4$, $R_5$, $R_6$ and Rc have the same meanings as in formula (I) and $R_7$ is a protecting group which is compatible with the reaction conditions used, and subsequent removal of the protecting group $R_7$.

c) reaction with compounds of formula

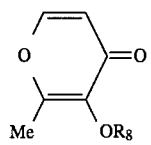

wherein $R_8$ is a protecting group which is compatible with the reaction conditions used.

Reaction a) is preferably carried out in inert solvents in the presence of condensins agents such as carbonyldiimidazole, dicyclohexylcarbodiimide, 1-hydroxybenzotriazole, at a temperatures ranging from −20° C. to the reflux temperature of the reaction mixture. Preferred solvents are tetrahydrofuran, dimethylformamide, acetonitrile.

Reaction b) is preferably carried out using carbonyldiimidazole in anhydrous tetrahydrofuran and silyl groups as protecting groups $R_7$, particularly terbutyldimethylsilyl group.

Reaction c) is preferably carried out in ethanol under reflux, usins as protecting group $R_8$, for example, a benzyl group, which can then be removed by catalytic hydrogenation or with other conventional methods for hydrogen transfer.

The compounds (I) resulting from reactions a), b) and c) can then be converted into other compounds (I), for example by means of salification and/or separation of the optical, geometric or diastereomeric isomers, according to conventional methods or by means of conversion of one of the groups R, $R_1$, $R_2$ and $R_3$ into another group R, $R_1$, $R_2$ and $R_3$ according to known reactions or reaction sequences.

Compounds of formula (II) are prepared by a process which consists in the reaction of a Michael accepter of formulae (VIa) or (VIb):

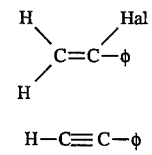
VIa $H-C\equiv C-\phi$
VIb where in Hal is a halogen atom (chlorine, bromine or iodine) and $\phi$ is an alkoxycarbonyl group or an electrophilic group which can be transformed into a carboxy or alkoxycarbonyl group with a 1,4-dihydropyridine of formula (VII)

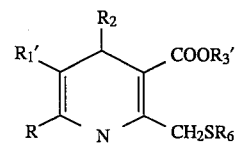
VII wherein R and $R_2$ are as defined above for formula (I); $R_1'$ and $R_3'$ have the same meanings as $R_1$ and $R_3$ except for a free or salified carboxy group or hydrogen, respectively;

$R_6$ is hydrogen, acetyl, benzoyl, or a group of formula $C(=NH)-NH_2$ or $C(=NH)-NH_2 \cdot H^+P^-$ wherein $P^-$ is the counter-ion of an inorganic or organic acid, such as hydrochloric, hydrobromic, acetic, camphorsulfonic, mandelic, tartaric, O,O-dibenzoyltartaric acids.

The reaction of compound (VI) with compound (VII), is generally carried out in an inert solvent and in the presence of a suitable base, giving the compounds of formula (VIII)

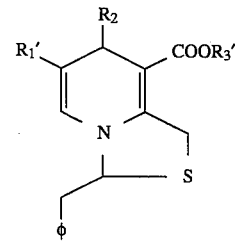
VIII wherein R, $R_1'$, $R_2$, $R_3'$ and $\phi$ are as defined above, in form of a sin,anti diastereomeric mixture, the sin diastereomer prevailing.

The resulting compounds of formula (VIII), both in form of single diastereomers and as diastereomeric mixtures, are transformed into compounds of formula (II), by reducing the free or esterified carboxylic group $\phi$ to primary alcohol which, after transformation into the corresponding halide or sulfonate or through the Mitsunobu reaction, can be converted into a $-NH_2$ group by reaction with an alkali azide and subsequent reduct ion; suitable reducing agents include diborane, an alkali or alkaline-earth metal borohydride, trialkyl- or triarylphosphines and the like.

The compounds of formula (I) in which n is different from 1, can be prepared with processes similar to those described above, starting from intermediates of formula (VIII) which are previously subjected to reactions for the elongation or shortening of the chain at the 3- position, according to well known methods.

Michael acceptors of formula (VI) are known or they can be prepared with conventional methods; some of them are also commercially available. Particularly, among the compounds of formula (VI), the following ones are mentioned:
a) propargyl acid esters or amides; b) α-haloacrylic esters or amides (obtainable from acrylic esters or amides by halogen addition and subsequent dehydrohalogenation).

1,4-Dihydropyridines of formula (VII) are known from WO87/00836 ( 12.02. 1987 ) or they can be prepared according to the methods described in said international application. Said compounds of formula (VII) can be used both in form of racemates and of pure enantiomers; an use fu 1 method for the preparation of the pure enantiomers of compounds of formula (VII) is disclosed in Italian patent application n. 19477 A/89 and it comprise s the optical resolution of the isothiouronium salts with optically active acids.

The acid of formula (III ) is known (T. Dobr et al., J.To.C.S., 105, 6505 (1983)).

The preparation of compounds (II) is also described in Italian patent application 20585 A/90.

The compounds of the invention turned out to be effective in preventing and/or decreasing the hyper-reactivity of the respiratory tract and in curing the phlogistic conditions which are related to acute e subchronical inflammation of bronchial mucosa.

Bronchial hyper-reactivity is a clinical symptom of asthma and it is believed to be a direct consequence of an abnormal and latent contractility and sensitivity of the bronchial mucosa.

Bronchial hyper-reactivity can cause acute crisis of asthma after physical practice, and/or after exposure to external stimuli such as the inhalation of fog, pollutants, allergens and autacoids.

The bronchial hyper-reactivity conditions may be simulated by an experimental model consisting in the PAF infusion ( 600 μg/l) in male guinea-pigs weighing 400–450 g, kept under forced ventilation under urethane and pancuronium bromide anesthesia.

PAF, which is one of the most important mediators involved in the inflammatory process of the airways, after infusion for 1 hour, causes an hyperreactivity reaction (bronchocostriction) to specific and different substances.

The activity of the compounds of the invention, in the considered pharmacological model, is shown by the prevention of the PAF-induced hyper-reactivity, measured as increase of the pulmonary insufflatory pressure (measured according to the modified procedure of Konzett and Rossler, Naun. Schmied. Arch. Exper. Pathol. Pharmacol. 191, 71, 1970).

The compounds of the invention, which are administered 10 minutes before the PAF administration in dosages which vary between 2 and 50 μg/kg, demonstrate a protective action which lasts at least 4–6 hours and results in a reduction of the PAF-induced hyperreactivity. Such pharmacological effects are dose related.

The compounds of the invention are also tested according to another experimental model, namely the Late Phase Reaction on sensitized guinea pigs (P. A. Hutson et al., Am. Rev. Respir. Dis. 137; (1988); 548–577. The Late Phase Reaction is characterized by an increase in bronchoalveolar lavage (BAL) of the number of eosinophils in guinea pigs sensitized to ovalbumin aerosol. The compounds of the invention are effective in reducing the number of eosinophils in BAL, which was made 72 hours after the ovalbumin challenge.

From what has been shown above it is clear that the compounds of the invention can be used in human therapy in the treatment of asthmatic and obstructive conditions of the respiratory tract, in the treatment of inflammatory phlogosis. For the intended therapeutic uses, the compounds of the invention will be administered in the form of pharmaceutical compositions which can be prepared with conventional excipients and techniques such as, for example, those described in Remington's Pharmaceutical Sciences Handbook, Mack Pub. Co., N.Y., USA, 17th ed., 1985, adapted for administration by intramuscular, intravenous, oral, aerosol and rectal routes.

The daily dose will depend on several factors such as the gravity of the pathology and the condition of the patient: it will normally consist of 1 to 50 mg of a compound of formula (I) for a patient weighing 70 kg, one or more times a day.

PREPARATION 1

To a suspension of S-[(6-methyl-5-methoxycarbonyl-3-ethoxycarbonyl-4-(3-nitrophenyl )-1,4-dihydropyridin-2-yl)methyl]isothiouronium chloride (20 g) in MeOH (200 ml), methyl propiolate (4.2 ml) and aqueous NaOH (35%, 10.8 ml) are added in this order under inert gas atmosphere at room temperature and under stirring. After complete dissolution of the reagents, a crystalline precipitate forms which is redissolved by addition of DMF (40 ml). Stirring is continued for 12 more hours, during which a second precipitate forms. This latter is filtered to give 14.6 g of methyl 2-(3-(5-methyl-6-methoxycarbonyl- 7-(3-nitrophenyl)-8-ethoxycarbonyl )-[ 3H,7H]thiazole[3,4-a]pyridinyl)acetate, m.p. 158°– 160° C.

PREPARATION 2

1 Liter of a sodium bicarbonate saturated aqueous solution is dropped into a suspension of 50 g of (7R)-S-[ (6-methyl- 5-methoxycarbonyl- 3-ethoxycarbonyl -4-(3-nitrophenyl)- 1,4-dihydropyridin-2-yl) methyl]isothiouronium-D(–)-mandelate in 1 l of AcOEt, under rapid stirring. At the end of the addition, the aqueous phase is removed, whereas the organic phase is dried over sodium sulfate and solvent is evaporated off under reduced pressure, keeping temperature below 40° C.

The residual crude (7R)-S-[(6-methyl-5-methoxycarbonyl- 3-ethoxycarbonyl-4-(3-nitrophenyl)-1,4-dihydropyridin- 2-yl)methyl]isothioureide (37 g) is dissolved in 150 ml of methanol and quickly added with 9 ml of methyl propiolate, under mechanical stirring and inert gas atmosphere, and immediately after that with 35% aqueous NaOH (11.3 ml). Precipitation of the product takes place nearly immediately. After 15 minutes the reaction mixture is added with 37% hydrochloric acid to acid pH, then the crystalline solid is filtered and dried, to obtain 40.2 g of methyl (7R)-3-[(6-methyl-5-methoxycarbonyl- 3-ethoxycarbonyl-4-(3-nitrophenyl) -1,4-dihydropyridin- 2-yl )methylthio]acrylate.

To a solution of 40.2 g of methyl (7R)-3-[(6-methyl-5-methoxycarbonyl-3-ethoxycarbonyl-4-(3-nitrophenyl)-1,4-dihydropyridin-2-yl)methylthio]acrylate in 110 ml of anhydrous DMF, 12.8 ml of 1,8-diazabicyclo[ 5.4.0]undec-7-ene (DBU) are added, under stirring and inert gas atmosphere. Stirring is continued for 18 more hours, then the reaction mixture is cooled with water/ice and added with 37% hydrochloric acid to acid pH. The crystalline precipitate is separated by filtration, to obtain 35.7 g of methyl (7R)-2-(3-(5-methyl-6-methoxycarbonyl- 7-( 3-nitrophenyl )-8-ethoxycarbonyl)-[ 3H,7H]thiazole[3,4-a]pyridinyl)acetate, m.p. 126°– 128° C.

PREPARATION 3

6.4 g of methyl (7R)-2-(3-(5-methyl-6-methoxycarbonyl-7-(3-nitrophenyl)-8-ethoxycarbonyl)[3H, 7H ] thiazole[ 3,4-a ]pyridinyl) acetate are added under stirring to a suspension of LiBr ( 3.8 g ) and sodium borohydride (1.75 g)

in diglyme (10 ml), which has been previously kept at room temperature for 30 minutes. The reaction mixture is heated to 50° C. for one hour, then it is poured into water and acidified with 1N hydrochloric acid. After extraction with AcOEt (3×15 ml ), the combined organic extracts are washed repeatedly with water (5×20 ml), dried over sodium sulfate and solvent is evaporated off under reduced pressure, to give 4.8 g of (7R)- 2-(3-(5-methyl-6-methoxycarbonyl-7-(3-nitrophe-nyl ) -8ethoxycarbonyl) [3H,7H]thiazole[3,4-a]pyridinyl)-ethanol, m.p. 58°–62° C., $[\alpha]_D = -51.9°$ (c=0.21 in EtOH).

PREPARATION 4 a) 25.2 ml of trifluoroacetic acid are dropped into a solution of 19 g of (7R)-2-(3-(5-methyl-6-methoxycarbonyl-7-(3-nitrophenyl)-8-ethoxycarbonyl) [3H,7H]thiazole[3,4-a]pyridinyl)ethanol, 25.8 g of triphenylphosphine and 21 g of sodium azide in 200 m! of DMF, cooled to 0° C. with water/ice, under stirring and inert gas atmosphere. The reaction mixture is kept at 0° C. under stirring for 10 minutes; then 18.4 ml of diethyl azadicarboxylate are added. After 5 more minutes, the reaction mixture is alkalinized with 1N NaOH and extracted with AcOEt (3×60 ml). The combined organic extracts are repeatedly washed with water (3×40 ml ) and dried over sodium sulfate, then solvent is evaporated off under reduced pressure. The crude product (50 g) is purified by silica gel chromatography (1000 g silica, eluent AcOEt/hexane 2/8), to obtain 16.5 g of (7R)-2-(3-(5-methyl-6-methoxycarbonyl-7-(3-nitrophenyl)-8-ethoxycarbo-nyl)[3H, 7H]thiazole[ 3,4-a] pyridinyl)ethylazide, m.p. 119°–120° C.

b) A solution of 16.5 g of (7R)-2-(3-(5-methyl-6-methoxycarbonyl- 7-(3-nitrophenyl)-8-ethoxycarbonyl)[ 3H,7H] thiazole[3,4-a]pyridinyl)ethylazide and 12.1 ml of triethylphosphite in 150 ml of toluene is kept under stirring and inert gas atmosphere for 24 hours, then the reaction mixture is saturated with hydrochloric acid gas (bubbling time: about 3 hours). After about 18 hours, a crystalline solid precipitates which is filtered, resuspended in 80 ml of methylene chloride and treated with 100 ml of a sodium bicarbonate saturated aqueous solution. The resulting organic solution is washed with water (3×30 ml) , dried over sodium sulfate and solvent is evaporated off under reduced pressure, to obta in 14 g of (7R)-2-(3-(5-methyl-6-methoxycarbonyl-7-(3-nitrophenyl)- 8-ethoxycarbonyl)[3H,7H] thiazole[3,4-a] pyridinyl)ethylamine, as a yellow oil.

PREPARATION 5

Following the procedure described in preparations 2, 3 and 4, the following 2-([3H,7H]thiazole[3,4-a] pyridin-3-yl)ethylamines are obtained:

5-methyl-6-methoxycarbonyl-7-(3-chlorophenyl )-8-ethoxycarbonyl, 5-methyl-6-methoxycarbonyl-7-(2,3-dichlorophenyl ) -8-ethoxycarbonyl, 5-methyl-6-methoxycarbonyl-7-phenyl-8-ethoxycarbonyl, 5-methyl-6-methoxycarbonyl-7-cyclohexyl-8-ethoxycarbonyl, 5-methyl-6-methoxycarbonyl-7-cyclopropyl-8-ethoxycarbonyl, 5-methyl-6-cyano-7-(3-nitrophenyl)-8-ethoxycarbonyl, 5-methyl-6-cyano-7-(3-chlorophenyl)-8-ethoxycarbonyl, 5-methyl-6-cyano-7-(2,3-dichlorophenyl)-8-ethoxycarbonyl, 5-methyl-6-cyano-7-phenyl-8-ethoxycarbonyl, 5-methyl-6-cyano-7-cyclohexyl-8-ethoxycarbonyl, 5-methyl-6-cyano-7-cyclopropyl-8-ethoxycarbonyl, 5-methyl-6-allyloxycarbonyl-7-(3-hitrophenyl)-8-ethoxycarbonyl, 5-methyl-6-allyloxycarbonyl-7-(3-chlorophenyl)-8-ethoxycarbonyl, 5-methyl-6-allyloxycarbonyl-7-(2,3-dichlorophenyl )-8-ethoxycarbonyl, 5-methyl-6-allyloxycarbonyl-7-phenyl-8-ethoxycarbonyl, 5-methyl-6-allyloxycarbonyl-7-cyclohexyl-8-ethoxycarbonyl, 5-methyl-6-allyloxycarbonyl-7-cyclopropyl-8-ethoxycarbonyl.

PREPARATION 6 a ) A mixture of ethyl 4-chloro-3-oxo-butanoate ( 57.3 ml) , cyclohexylaldehyde (53.65 ml ) , acetic acid ( 2.75 ml) and benzylamine (4.38 ml) is kept for 24 hours at room temperature, then it is diluted with 150 ml of AcOEt and washed with 100 ml of water, then with a $NaH_2PO_4$ saturated solution. Solvent is evaporated off to obtain 108.43 g of 4-chloro-3-oxo-2-ethoxycarbonyl- 1-cyclohexylbut-1-ene.

b) A solution of the compound obtained in a) (60 g ) and methyl 3-aminocrotonate (26.7 g) in acetonitrile (500 ml) is heated for 3 hours to 60 ° C., cooled to 35° C., then added with p-toluenesul fonic acid to pH-1. After stirring for 30 more minutes, acetonitrile is evaporated off and the residue is taken up into 300 ml of diethyl ether and 300 ml of water. Phases are separated, and, after evaporation of the solvent and crystallization, 75.1 g of (R,S)-2-chloromethyl-3-ethoxycarbonyl- 4-cyclohexyl-5-methoxycarbonyl-6-methyl-1,4-dihydropyridine are obtained, m.p. 103°–105° C.

c) A solution of 6 g of the compound obtained in b) and thiourea (1.35 g) in ethanol (40 ml) is refluxed for 2 hours.

After cooling, the crystalline precipitate of (R,S)-[(3-ethoxycarbonyl-4-cyclohexyl-5-methoxycarbonyl- 6-methyl-1,4-dihydropyridin )methyl]isothiouronium chloride (6.9 g, m.p. 201°–203° C.) is recovered by filtration.

Analogously, by reacting thiourea with a 2 -chloromethyldihydropyridine obtained from methyl 3-aminocrotonate and a suitable 1-substituted 4-chloro-3-oxo-2-ethoxycarbonylbut- 1-ene, the following compounds are obtained:

(R,S)-[(3-ethoxycarbonyl-4-cyclopropyl-5-methoxycarbonyl- 6-methyl-1,4-dihydropyridin)methyl]isothiouronium chloride, (R,S)-[(3-ethoxycarbonyl-4-cyclobutyl-5-methoxycarbonyl- 6-methyl-1,4-dihydropyridin)methyl]isothiouronium chloride, (R,S)-[(3-ethoxycarbonyl-4-cyclopentyl-5-methoxycarbonyl- 6-methyl-1,4-dihydropyridin)methyl]isothiouronium chloride, (R,S)-[(3-ethoxycarbonyl-4-cycloheptyl-5-methoxycarbonyl- 6-methyl-1,4-dihydropyridin)methyl]isothiouronium chloride.

PREPARATION 7

By reacting thiourea with the suitable 2-chloromethyldihydropyridines, which are prepared in their turn using 3-amino-3-methylacrylonitrile or allyl 3-aminocrotonate and the suitable 1-substituted 4-chloro- 3-oxo-2-ethoxycarbonyl-l-butenes in the process of preparation 6, the following compounds are prepared:

- (R,S)-[(3-ethoxycarbonyl-4-cyclohexyl-5-cyano-6-methyl- 1,4-dihydropyridin)methyl]isothiouronium chloride,
- (R,S)-[(3-ethoxycarbonyl-4-cyclopropyl-5-cyano-6-methyl- 1,4-dihydropyridin)methyl]isothiouronium chloride,
- (R,S)-[(3-ethoxycarbonyl-4-cyclobutyl-5-cyano-6-methyl- 1,4-dihydropyridin)methyl]isothiouronium chloride,
- (R,S)-[(3-ethoxycarbonyl-4-cyclopentyl-5-cyano-6-methyl-1,4-dihydropyridin)methyl]isothiouronium chloride,
- (R,S)-[(3-ethoxycarbonyl-4-cycloheptyl-5-cyano-6-methyl- 1,4-dihydropyridin)methyl]isothiouronium chloride,
- (R,S]-[(3-ethoxycarbonyl-4-cyclohexyl-5-allyloxycarbony 1-6-methyl-1,4-dihydropyridin)methyl]isothiouronium chloride,
- (R,S)-[(3-ethoxycarbonyl-4-cyclopropyl-5-allyloxycarbony 1-6-methyl-1,4-dihydropyridin)methyl]isothioutonium chloride,
- (R,S)-[(3-ethoxycarbonyl-4-cyclobutyl-5-allyloxycarbonyl- 6-methyl-1,4-dihydropyridin)methyl]isothiouronium chloride,
- (R,S)-[(3-ethoxycarbonyl-4-cyclopentyl-5-allyloxycarbonyl- 6-methyl-1,4-dihydropyridin)methyl]isothiouronium chloride,
- (R,S)-[(3-ethoxycarbonyl-4-cycloheptyl-5-allyloxycarbonyl- 6-methyl-1,4-dihydropyridin)methyl]isothiouronium chloride.

PREPARATION 8

A solution of 1.16 g of potassium bicarbonate in water (50 ml ) is added with a solution of (R,S)-[ (3-ethoxycarbonly-4-cyclohexyl-5-methoxycarbonyl-6-methyl - 1,4-dihydropyridin)methyl]isothiouronium chloride (5 g) in AcOEt (100 ml) at room temperature and under strong stirring. After 10 minutes the phases are separated and the aqueous one is extracted with AcOEt (2×25 ml).

The combined organic phases are washed with a NaCl saturated solution and dried over sodium sulfate. After evaporation of the solvent, by crystallization from ethyl ether, 3.6 g of (R,S)-[ (3-ethoxycarbonyl-4-cyclohexyl-5-methoxycarbonyl-6-methyl-1,4-dihydropyridin)methyl] isothioureide are obtained, m.p. 141°–143° C. 3.6 g of the obtained isothioureide are refluxed in 500 ml of acetonitrile with 3.43 g of O,O'-dibenzoyl-D-tartaric acid for 1 hour. The mixture is then left at room temperature for 1 night: 1.86 g of bis-(+)-[(3-ethoxy-carbonyl- 4-cyclohexyl-5-methoxycarbonyl-6-methyl-1,4-dihydropyridin)methyl] isothiouronium O,O'-dibenzoyl-D-tartrate crystallizes, m.p. 174°–177° C.

Chiral isothioureas as the free bases are obtained from the chiral isothiouronium salts by treatment with sodium bicarbonate solutions, anal ogously to the process described at the beginning of this preparation. (+)-[(3-Ethoxycarbonyl-4-cyclohexyl-5-methoxycarbonyl- 6-methyl-1,4-dihydropyridin)methyl]isothioureide $[\alpha]_D = 65°$ and (−)-[(3-ethoxycarbonyl-4-cyclohexyl-5-methoxycarbonyl- 6-methyl-1,4-dihydropyridin)methyl]isothioureide $[\alpha]_D -62°$ were obtained.

EXAMPLE 1

A solution of trolox$^{(R)}$ (690 mg) in 5 ml of THF, under stirring, in inert gas atmosphere and at room temperature, is added with 470 mg of carbonyldiimidazole in portions. After 2 hours, the reaction mixture is added with a solution of 1.13 g of (7R)-2-(3-(5-methyl-6-methoxyca rbonyl-7-(3-nitrophenyl)-8-ethoxycarbonyl)[ 3H,7H]thiazole[3,4-a]pyridinyl)ethylamine in 7 ml of THF. After 2 more hours, the reaction mixture is poured into 20 ml of water and extracted with AcOEt (3×10 ml). The combined organic extracts are dried over sodium sulfate and solvent is evaporated off under reduced pressure. The resulting crude product is purified by silica gel chromatography (50 g silica, changeable eluent AcOEt/hexane 6/4 - AcOEt/hexane 1/1) to obtain, after crystallization from hexane/isopropyl ether, 95/5, 1.3 g of (7R)-N-[((5-methyl-6-methoxycarbonyl- 7-(3-nitrophenyl)-8-ethoxycarbonyl)[3H, 7H ]thiazole[ 3,4-a ]pyridin-3-yl)ethyl ]-6-hydroxy-2,5,7,8-tetramethylchroman- 2-yl -carboxyamide, m.p. 71°–75° C.

EXAMPLE 2

Following the procedure described in example 1, the following N-[([3H,7H]thiazole [3,4-a ]pyridin-3-yl)ethyl] -6-hydroxy-2,5,7,8-tetrametylchroman-2-ylcarboxyamides are prepared:

- 5-methyl-6-methoxycarbonyl-7-(3-chlorophenyl)-8-ethoxy-carbonyl,
- 5-methyl-6-methoxycarbonyl-7-(2,3-dichlorophenyl)-8-ethoxycarbonyl, m.p. 63°–66° C.,
- 5-methyl-6-methoxycarbonyl-7-phenyl-8-ethoxycarbonyl,
- 5-methyl-6-methoxycarbonyl-7-cyclohexyl-8-ethoxycarbonyl, m.p. 58°–60° C.,
- 5-methyl-6-methoxycarbonyl-7-cyclohexyl-8-ethoxycarbonyl,
- 5-methyl-6-cyano-7-(3-nitrophenyl)-8-ethoxycarbonyl,
- 5-methyl-6-cyano-7-(3-chlorophenyl)-8-ethoxycarbonyl,
- 5-methyl-6cyano-7-(2,3-dichlorophenyl)-8-ethoxycarbonyl, m.p. 77°–80° C.,
- 5-methyl-6-cyano-7-phenyl-8-ethoxycarbonyl,
- 5-methyl-6-cyano-7-cyclohexyl-8-ethoxycarbonyl,
- 5-methyl-6-cyano-7-cyclopropyl-8-ethoxycarbonyl,
- 5-methyl-6-allyloxycarbonyl-7-(3-nitrophenyl)-8-ethoxycarbonyl, m.p. 69°–72°C.,
- 5-methyl-6-allylooxycarbonyl-7-(3-chlorophenyl)-8-ethoxycarbonyl,
- 5-methyl-6-allyloxycarbonyl-7-(2,3-dichlorophenyl)-8-ethoxycarbonyl,
- 5-methyl-6-allyloxycarbonyl-7-phenyl-8-ethoxycarbonyl,
- 5-methyl-6-allyloxycarbonyl-7-cyclohexyl-8-ethoxycarbonyl,
- 5-methyl-6-allyloxycarbonyl-7-cyclopropyl-8-ethoxycarbonyl.

EXAMPLE 3

A solution of 3 g of (7R)-2-(3-(5-methyl-6-methoxycarbonyl- 7-(3-nitrophenyl)-8-ethoxycarbonyl) [3H,7H]thiazole[3,4-a]pyridinyl)ethylamine in 40 ml of acetonitrile is added with 1.81 g of 1-hydroxybenzotriazole, 1.09 g of 2,3-dihydroxybenzoic acid and 1.93 ml of N-methylmorpholine. The resulting reaction mixture, cooled to −5° C., is added, under stirring and inert gas atmosphere, with a solution of 2.57 g of 1-ethyl-3-(3-dimethylaminopropyl) carbodiimide hydrochloride in 40 ml of THF. After 48 hours the reaction mixture is poured into 150 ml of a sodium bicarbonate saturated aqueous solution and repeatedly extracted with AcOEt (3×30 ml ). The combined organic extracts are washed first with 1N hydrochloric acid (20 ml ), then with water (3×30 ml ), dried over sodium sulfate and solvent is evaporated off under reduced pressure. The residue is purified by silica gel chromatography (100 g silica, eluent AcOEt/petroleum ether/AcOH 4/16/1) to obtain, after crystallization from toluene/isopropyl ether 1/1, 3.2 g of (7R)-N-[((5-methyl- 6-methoxycarbonyl-7-(3-nitrophenyl)-8-ethoxycarbonyl ) [ 3H, 7H ]thiazole [ 3,4-a ] pyridin-3-yl ) ethyl ]-2,3-dihydroxyphenylcarboxyamide, m.p. 149°–150° C.

EXAMPLE 4

Following the procedure described in example 3 and using the suitable substituted benzoic acids, the following compounds are obtained:

N- [((5-methyl-6-methoxycarbonyl-7-(3-chlorophenyl)-8-ethoxycarbonyl) [3H,7H ]thia zole[ 3,4-a ]pyridin-3-yl)ethyl] -2,3-dihydroxyphenylcarboxyamide, m.p. 141°–142° C., N-[((5-methyl-6-methoxycarbonyl-7-phenyl-8-ethoxycarbonyl) [3H,7H ]thiazole [3,4-a ]pyridin-3-yl)ethyl]-2,3-dihydroxyphenylcarboxyamide, N-[((5-methyl-6-methoxycarbonyl-7-cyclohexyl-8-ethoxycarbonyl) [3H,7H ]thiazole [3,4-a]pyridin-3-yl) ethyl]-2,3-dihydroxyphenylcarboxyamide, m.p. 133°–135° C., N- [((5-methyl-6-cyano-7-(3-nitrophenyl) -8-ethoxycarbonyl) [3H, 7H]thiazole [3,4-a]pyridin-3-yl)ethyl ] -2,3-dihydroxyphenylcarboxyamide, N-[((5-methyl-6-cyano-7-(3-chlorophenyl)-8-ethoxycarbonyl) [3H,7H ]thiazole[3,4-a]pyridin-3-yl)ethyl ]-2,3-dihydroxyphenylcarboxyamide, m.p. 167°–170° C., N-[((5-methyl-6-cyano-7-cyclohexyl-8-ethoxycarbonyl) [3H,7H]thiazole[3,4-a]pyridin-3-yl)ethyl]-2,3-dihydroxyphenyl carboxyamide, N-[((5-methyl-6-allyloxycarbonyl-7-(3-nitrophenyl )-8ethoxycarbonyl) [3H,7H]thiazole [3,4-a]pyridin-3-yl)ethyl] -2,3-dihydroxyphenylcarboxyamide, m.p. 153°–155° C., N-[((5-methyl-6-allyloxycarbonyl-7-(3-chlorophenyl )-8ethoxycarbonyl) [3H,7H]thiazole[3,4-a]pyridin-3-yl) ethyl] -2,3-dihydroxyphenylcarboxyamide, N-[((5-methyl-6-allyloxycarbonyl-7-cyclohexyl-8-ethoxycarbonyl) [3H,7H]thiazole[3,4-a]pyridin-3-yl) ethyl]-2,3-dihydroxyphenylcarboxyamide, N-[((5-methyl-6-methoxycarbonyl-7-(3-nitrophenyl)-8ethoxycarbonyl) [3H,7H]thiazole[3,4-a]pyridin-3-yl) ethyl] -3,4-dihydroxyphenylcarboxyamide, m.p. 160°–161° C., N-[((5-methyl-6-methoxycarbonyl-7-cyclohexyl-8-ethoxycarbonyl) [3H,7H]thiazole [3,4-a]pyridin-3-yl) ethyl]-3,4-dihydroxyphenylcarboxyamide, N-[((5-methyl-6-cyano-7-(3-nitrophenyl)-8-ethoxycarbonyl) [3H,7H]thiazole[3,4-a]pyridin-3-yl)ethyl]-3,4-dihydroxyphenyl carboxyamide, N-[((5-methyl-6-cyano-7-(3-chlorophenyl)-8-ethoxycarbonyl) [3H,7H]thiazole[3,4-a]pyridin-3-yl)ethyl]-3,4-dihydroxyphenylcarboxyamide, N-[((5-methyl-6-allyloxycarbonyl-7-(3-nitrophenyl )-8-ethoxycarbonyl) [3H,7H]thiazole[3,4-a]pyridin-3-yl) ethyl] -3,4-dihydroxyphenylcarboxyamide, N-[((5-methyl-6-allyloxycarbonyl-7-(3-chlorophenyl )-8-ethoxycarbonyl) [3H,7H]thiazole[3,4-a]pyridin-3-yl)ethyl] -3,4-dihydroxyphenylcarboxyamide, (7R)-N-[((5-methyl-6-methoxycarbonyl-7-(3-nitrophenyl)- 8-ethoxycarbonyl)[3H,7H]thiazole[3,4-a]pyridin-3-yl)ethyl] -4-hydroxy-3 5-ditertbutylphenylcarboxy amide m.p. 204°–206° C., N-[((5-methyl-6-methoxycarbonyl-7-(3-chlorophenyl )-8-ethoxycarbonyl) [3H,7H]thiazole[3,4-a]pyridin-3-yl)ethyl] -4-hydroxy-3,5-ditertbutylphenylcarboxy amide, m.p. 190°–194° C., N-[((5-methyl-6-methoxycarbonyl-7-(2,3-dichlorophenyl) 8-ethoxycarbonyl)[3H,7H]thiazole[3,4-a]pyridin-3-yl)ethyl] -4-hydroxy-3,5-ditertbutylphenylcarboxy amide, N-[((5-methyl-6-methoxycarbonyl-7-phenyl-8-ethoxycarbonyl) [3H,7H]thiazole[3,4 -a]pyridin-3-yl)ethyl]-4-hydroxy- 3,5-ditertbutylphenyl carboxyamide, N-[((5-methyl-6-methoxycarbonyl-7-cyclohexyl-8-ethoxycarbonyl) [3H,7H]thiazole[3,4-a]pyridin-3-yl) ethyl]-4-hydroxy- 3,5-ditertbutylphenylcarboxyamide, m.p. 182°–184° C., N-[((5-methyl-6-cyano-7-(3-nitrophenyl )-8-ethoxycarbonyl) [3H,7H]thiazole[3,4-a]pyridin-3-yl)ethyl]-4-hydroxy- 3,5-ditertbutylphenylcarboxyamide, N- [((5-methyl-6-cyano-7-(3-chlorophenyl) -8-ethoxycarbonyl) [3H,7H ]thiazole[3,4-a]pyridin-3-yl)ethyl]-4-hydroxy- 3,5-ditertbutylphenylcarboxyamide, m.p. 200°–201° C., N-[((5-methyl-6-cyano-7-cyclohexyl-8-ethoxycarbonyl) [3H,7H]thiazole[3,4-a]pyridin-3-yl)ethyl]-4-hydroxy-3,5-ditertbutylphenylcarboxyamide, N-[((5-methyl-6-allyloxycarbonyl-7-(3-nitrophenyl )-8ethoxycarbonyl) [3H,7H]thiazole[3,4-a]pyridin-3-yl) ethyl] -4-hydroxy-3,5-ditertbutylphenylcarboxyamide, N-[((5-methyl-6-allyloxycarbonyl-7-(3-chlorophenyl )-8-ethoxycarbonyl) [3H,7H]thiazole[3,4-a]pyridin-3-yl) ethyl] -4 -hydroxy-3,5-ditertbutylphenyl carboxyamide, N-[((5-methyl-6-allyloxycarbonyl-7-cyclohexyl-8-ethoxycarbonyl) [3H,7]thiazole[3,4-a]pyridin-3-yl) ethyl]-4-hydroxy- 3,5-ditertbutylphenylcarboxyamide, N-[((5-methyl-6-methoxycarbonyl-7-(3-nitrophenyl )-8-ethoxycarbonyl) [3H,7H]thiazole [3,4 -a]pyridin-3-yl)ethyl] -4-hydroxy-3,5-diethylphenylcarboxyamide, m.p. 187°–190° C., N-[((5-methy1-6-methoxycarbonyl-7-cyclohexyl-8-ethoxycarbonyl) [3H,7H]thiazole[3,4-a]pyridin-3-yl) ethyl]-4-hydroxy- 3,5-diethylphenylcarboxyamide, N-[((5-methyl-6-cyano-7-(3-nitrophenyl) -8-ethoxycarbonyl) [3H,7H]thiazole[3,4-a]pyridin-3-yl)ethyl]-4-hydroxy- 3,5-diethylphenylcarboxyamide, N-[((5-methyl-6-allyloxycarbonyl-7-(3-nitrophenyl )-8ethoxycarbonyl) [3H,7H]thiazole[3,4-a]pyridin-3-yl) ethyl] -4-hydroxy-3,5-diethylphenylcarboxyamide, N-[((5-methyl-6-allyloxycarbonyl-7-(3-chlorophenyl )-8ethoxycarbonyl) [3H,7H]thiazole[3,4-a]pyridin-3-yl) ethyl] -4 -hydroxy-3,5-diethylphenylcarboxyamide.

EXAMPLE 5

A solution of 5 g of (7R) -2-3-(5-methyl-6-methoxycarbonyl- 7-(3-nitrophenyl) -8-ethoxycarbonyl) [3H,7H]-thiazole[ 3,4-a]pyridinyl)ethylamine in 40 ml of anhydrous THF is added with 1.9 g of carbonyldiimidazole in portions, under stirring and inert gas atmosphere. After 15 minutes, a solution obtained dissolving 3.13 g of 4-tertbutyldimethylsilyloxy-3,5,6-trimethylphenol in 30 ml of anhydrous THF is dropped therein, heating to 60° C., then 360 mg of sodium hydride ( 80% suspension in oil ) are added, keeping for 15 minutes under stirring.

After 30 minutes the reaction mixture is acidified with 1N hydrochloric acid and extracted with AcOEt (3×30 ml) . The combined organic extracts are washed with water (3×20 ml), dried over sodium sulfate and solvent is evaporated off under reduced pressure. The residue is purified by silica gel chromatography (100 g of silica, eluent ethyl ether/petroleum ether 1/1) , to obta in 5.2 g of (7R)-4-[ ( (5-methyl-6-methoxycarbonyl-7( 3-nitrophenyl)-8-ethcxycarbonyl) [3H,7H]thiazole[ 3,4-a] pyridin-3-yl)ethylaminocarbonyloxy]-2,3,6-trimethylphenol-O-tertbutyldimethylsilyl ether.

5.2 g of (7R)-4-[ ( (5-methyl-6-methoxycarbonyl-7-( 3-nitrophenyl)-8-ethoxycarbonyl)[3H,7H]thiazole[3,4-a] pyridin-3-yl)ethylaminocarbonyloxy]-2,3,6-trimethylphenol-O-tertbutyldimethylsilyl ether are dissolved in 30 ml of THF, then the reaction mixture is cooled to −10° C. and 6.6 ml of a 1.1M solution of tetrabutylammonium fluoride in THF are dropped into said solution. After 5 minutes the reaction mixture is quickly poured into 50 ml of a 1M hydrochloric acid solution and extracted with AcOEt (3×30 ml).

The combined organic extracts are washed with water (3×20 ml), dried over sodium sulfate and solvent is evaporated off under reduced pressure. The residue is purified by silica gel chromatography (150 g silica, eluent AcOEt/hexane 1/2) to give 4.7 g of (7R)-4-[((5-methyl- 6-methoxycarbonyl-7-(3-nitrophenyl)-8-ethoxycarbonyl) [3H,7H]thiazole[3,4-a]pyridin-3-yl) ethylaminocarbonyloxy] -2,3,6-trimethylphenol, 1H N.M.R. (200 MHz) d 1.25 (t, 3H) , 2.05 (m, 1H), 2.08 (s, 3H) , 2.17 (s, 3H), 2.2 (s, 3H), 2.35 (m, 1H), 2.6 (s, 3H) , 3.49 (m, 2H), 3.68 (s, 3H), 4.32 (m, 2H), 4.2 (d, 1H), 4.65 (d, 1H), 5.1 (s, 1H), 5.15 (s, 1H), 5.32 (t, 1H), 5.5 (m, 1H), 6.7 (s, 1H), 7.45 (t, 1H), 7.62 (d, 1H), 8.05 (m, 2H), m.p. 1906°–193° C.

EXAMPLE 6

Following the procedure described in example 5, starting from the suitable 0-tertbutyldimethylsilylhydroquinones, the following compounds are prepared:

4-[((5-methyl-6-methoxycarbonyl-7-(3-chlorophenyl) -8-ethoxycarbonyl) [3H, 7H]thiazole [3,4-a ]pyridin-3-yl) ethylaminocarbonyloxy] -2,3,6-trimethylphenol, m.p. 182°–185° C., 4-[((5-methyl-6-methoxycarbonyl-7-phenyl-8-ethoxycarbonyl) [3H,7H]thiazole[3,4-a]pyridin-3-yl)ethylaminocarbonyloxy] -2,3,6-trimethylphenol, 4- [((5-methyl-6-methoxycarbonyl-7-cyclohexyl-8-ethoxycarbonyl) [3H,7H]thiazole[3,4-a]pyridin-3-yl) ethylaminocarbonyloxy] -2,3,6-trimethylphenol, m.p. 176°–179° C., 4-[((5-methyl-6-cyano-7-(3-nitrophenyl)-8-ethoxycarbonyl) [3H,7H]thiazole[3, 4-a ]pyridin-3-yl )ethylaminocarbonyloxy] -2,3,6-trime thylphenol, 4-[((5-methyl-6-cyano-7-(3-chlorophenyl )-8-ethoxycarbonyl) [3H,7H]thiazole[3,4-a]pyridin-3-yl)ethylaminocarbonyloxy] -2,3,6-trimethylphenol, 4-[((5-methyl-6-cyano-7-cyclohexyl-8-ethoxycarbonyl) [3H,7H]thiazole[3,4-a]pyridin-3-yl) ethylaminocarbonyloxy]-2,3,6-trimethylphenol, 4-[((5-methyl-6-allyloxycarbonyl-7-(3-nitrophenyl)-8ethoxycarbonyl) [3H,7H]thiazole[3,4-a]pyridin-3-yl) ethylaminocarbonyloxy]-2,3,6-trimethylphenol, 4-[((5-methyl-6-allyloxycarbonyl-7-(3-chlorophenyl)-8ethoxycarbonyl) [3H,7H]thiazole[3,4-a]pyridin-3-yl) ethy laminocarbonyloxy]-2,3,6-trimethylphenol, 4-[((5-methyl-6-allyloxycarbonyl-7-cyclohexyl-8-ethoxycarbonyl) [3H,7H]thiazole [3,4-a]pyridin-3-yl) ethylaminocarbonyloxy] -2,3,6-trimethylphenol, 4-[((5-methyl-6-methoxycarbonyl-7-(3-nitrophenyl )-8ethoxycarbonyl) [3H,7H]thiazole[3,4-a]pyridin-3-yl) ethylaminocarbonyloxy] -2,3,6-triethylphenol, m.p. 196°–198° C., 4-[((5-methyl-6-methoxycarbonyl -7-(3-chlorophenyl)-8ethoxycarbonyl) [3H,7H]thiazole[3,4-a]pyridin-3-yl) ethylaminocarbonyloxy] -2,3,6-triethylphenol, 4-[((5-methyl-6-methoxycarbonyl -7-cyclohexyl-8-ethoxycarbonyl) [3H,7H]thiazole[3,4-a]pyridin-3-yl) ethylaminocarbonyloxy] -2,3,6-triethylphenol, 4-[((5-methyl-6-cyano-7-(3-nitrophenyl) -8-ethoxycarbonyl) [3H,7H]thiazole[3,4-a ]pyridin-3-yl)ethylaminocarbonyloxy] -2,3,6-triethylphenol, 4-[((5-methyl-6-cyano-7-cyclohexyl-8-ethoxycarbonyl) [3H,7H]thiazole[3,4-a]pyridin- 3-yl)ethylaminocarbonyloxy] -2,3,6-triethylphenol, 4-[((5-methyl-6-allyloxycarbonyl-7-(3-nitrophenyl)-8-ethoxycarbonyl) [3H,7H]thiazole[3,4-a]pyridin-3-yl) ethylaminocarbonyloxy]-2,3,6-triethylphenol, 4-[((5-methyl-6-allyloxycarbonyl-7-(3-chlorophenyl)-8ethoxycarbonyl) [3H,7H]thiazole[3,4-a]pyridin-3-yl) ethylaminocarbonyloxy] -2,3,6-triethylphenol, 4-[((5-methyl-6-methoxycarbonyl-7-(3-nitrophenyl )-8ethoxycarbonyl) [3H,7H]thiazole[3,4-a]pyridin-3-yl) ethylaminocarbonyloxy] -2,6-ditertbutyl-3-methylphenol, m.p. 215°–218° C., 4 -[((5-methyl-6-methoxycarbonyl-7-(3-chlorophenyl ) -8-ethoxycarbonyl) [3H,7H]thiazole[3,4-a]pyridin-3-yl)ethylaminocarbonyloxy] -2,6-ditertbutyl-3-methylphenol, 4-[((5-methyl-6-methoxycarbonyl-7-cyclohexyl-8-ethoxycarbonyl) [3H,7H]thiazole[3,4-a] pyridin-3-yl)ethylaminocarbonyloxy)]-2,6-ditertbutyl-3-methylphenol, 4-[((5-methyl-6-cyano-7-(3-nitrophenyl)-8-ethoxycarbonyl) [3H,7H]thiazole[3,4-a]pyridin-3-yl)ethylaminocarbonyloxy] -2,6-ditertbutyl-3-methylphenol, 4-[((5-methyl-6-cyano-7-cyclohexyl-8-ethoxycarbonyl) [3H, 7H]thiazole[3,4-a]pyridin-3-yl)ethylaminocarbonyloxy)]-2,6-ditertbutyl-3-methylphenol, 4-[((5-methyl-6-allyloxycarbonyl-7-(3-nitrophenyl ) -8-ethoxycarbonyl) [3H,7H]thiazole[3,4-a]pyridin-3-yl)ethylaminocarbonyloxy] -2,6-ditertbutyl-3-methylphenol, 4-[((5-methyl-6-allyloxycarbonyl-7-(3-chlorophenyl ) -8ethoxycarbonyl) [3H,7H]thiazole[3,4-a]pyridin-3-yl) ethylaminocarbonyloxy]-2,6-ditertbutyl-3-methylphenol.

We claim:

1. Compounds of general formula (I)

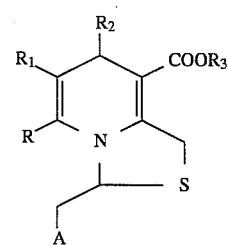

wherein:

R is $(C_1-C_4)$ alkyl;

$R_1$ is a cyano, free or salified carboxy, $(C_1-C_6)$ alkoxycarbonyl group or a group of formula $-CONH(CH_2)_qNR_aR_b$ wherein q is an integer from 2 to 4; $R_a$ is hydrogen, $(C_1-C_6)$ alkyl, benzyl; $R_b$ is hydrogen or $(C_1-C_6)$ alkyl;

$R_2$ is a $(C_3-C_7)$-cycloalkyl, α-, β-, or γ-pyridyl, or optionally substituted phenyl;

$R_3$ is hydrogen, a pharmaceutically acceptable cation or $(C_1-C_6)$ alkyl;

A is a group of formula:

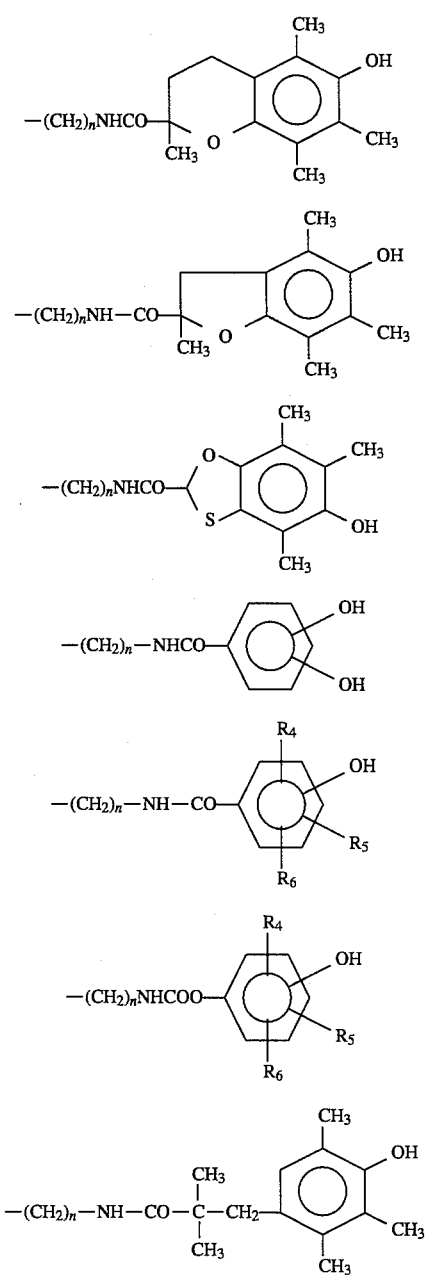

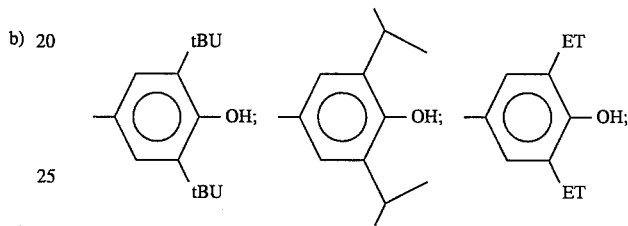

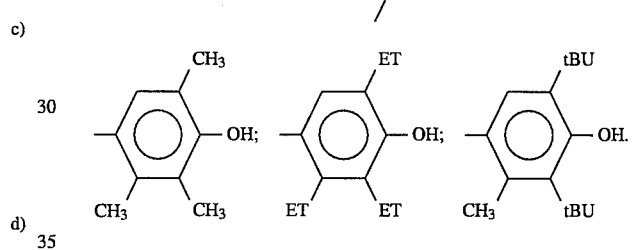

$R_4$, $R_5$ and $R_6$ are straight or branched $(C_1-C_4)$ alkyl or one of them is hydrogen and the other are straight or branched $(C_1-C_4)$ alkyl; or one of them is $-CH_2NRaRb$, being Ra, Rb as defined above; Rc is $(C_1-C_4)$ alkyl; n is zero or an integer from 1 to 3;

and the pharmaceutically acceptable salts thereof, the single enantiomers, racemates, diastereomers and the mixtures thereof.

2. Compounds according to claim 1 wherein n is the integer 1.

3. Compounds according to claim 1 wherein A is a group of formula d) bearing the two OH groups at the 2,3- or 3,4-positions of the phenyl ring.

4. Compounds according to claim 1 wherein A is a group of formulae e) and f) selected from:

5. Compounds according to claim 1 wherein $R_1$ is selected from cyano, methoxycarbonyl, ethoxycarbonyl, allyloxycarbonyl groups, a group of formula $-CONH(CH_2)_qNRaRb$, wherein q, Ra and Rb are as defined above; $R_2$ is an optionally substituted phenyl group or a $(C_3-C_7)$ alkyl group, as defined above, R is methyl and $R_3$ is $(C_1-C_6)$ alkyl.

6. Compounds according to claim 1 wherein $R_1$ is an alkoxycarbonyl group; $R_2$ is an optionally substituted phenyl; R is methyl and $R_3$ is $(C_1-C_6)$ alkyl.

7. Pharmaceutical compositions containing as the active ingredient one compound of formula (I).

8. A method of treating asthmatic and inflammatory conditions in a patient in need of such treatment, comprising administering an antiasthmatic or antiinflammatory effective amount of the compound of claim 1 to a patient in need of such treatment.

9. A method of preventing or decreasing the hyperactivity of the respiratory tract in a patient in need of such treatment, comprising administering an antihyperactivity effective amount of the compound of claim 1 to patient in need of such treatment.

* * * * *